United States Patent
Selmer-Olsen

(10) Patent No.: US 6,905,716 B2
(45) Date of Patent: Jun. 14, 2005

(54) PROPIONIC ACID BASED PRESERVATIVE AGENT FOR ANIMAL AND VEGETABLE PRODUCTS

(75) Inventor: Eirik Selmer-Olsen, Son (NO)

(73) Assignee: TINE Norske Meierier BA, Oslo (NO)

( * ) Notice: Subject to any disclaimer, the term of this patent is extended or adjusted under 35 U.S.C. 154(b) by 199 days.

(21) Appl. No.: 10/332,904

(22) PCT Filed: Jul. 10, 2001

(86) PCT No.: PCT/NO01/00297

§ 371 (c)(1),
(2), (4) Date: Jan. 15, 2003

(87) PCT Pub. No.: WO02/16629

PCT Pub. Date: Feb. 28, 2002

(65) Prior Publication Data

US 2004/0033289 A1 Feb. 19, 2004

(30) Foreign Application Priority Data

Jul. 25, 2000 (NO) ............................................ 20003801

(51) Int. Cl.$^7$ .......................... C12P 7/52; A23C 21/02; A23K 3/03
(52) U.S. Cl. ......................... 426/43; 426/335; 426/532
(58) Field of Search .............................. 426/43, 61, 54, 426/335, 532, 654; 435/42, 176, 177, 182, 252.4, 252.9

(56) References Cited

FOREIGN PATENT DOCUMENTS

| CA | 1 218 894 | 3/1987 |
|---|---|---|
| EP | 0 160 417 | 11/1985 |
| SE | 806718 | 3/1982 |

OTHER PUBLICATIONS

Biotechnology and Bioengineering, vol. 42, 1993, Agnes Colomban: Production of Propionic Acid from Whey Permeate by Sequential Fermentation, Ultrafiltration, and Cell Recycling, pp. 1091–1098.
WPI/Derwent's abstract, Accession No. 1976–47526, week 7625, Abstract of SU492268, (Butter Cheese Ind), Dec. 10, 1975.
Biosis, Prev199698774867, vol. 51, No. 2, Begin A. et al: "Production of mycostatic whey by Propionibacterium shermanii immobilized in alginate gels", 1996, pp. 73–78.
WPI/Derwent's abstract, Accession No. 1981–16829, week 8110, Abstract of SU745482, (Latv Agric Acad), Jul. 8, 1980.

*Primary Examiner*—Keith Hendricks
(74) *Attorney, Agent, or Firm*—Young & Thompson

(57) ABSTRACT

The present invention relates to a preservative agent based on propionic acid, suitable for animal and vegetable products, and to the preparation and use of the same. The preservative agent is obtained by fermentation of whey or components of whey.

13 Claims, 3 Drawing Sheets

PROPIONIC ACID BASED PRESERVATIVE AGENT FOR ANIMAL AND VEGETABLE PRODUCTS

BACKGROUND OF THE INVENTION

The present invention relates to a preservative agent suitable for animal and vegetable products and to the preparation and use of the same. The preservative agent is obtained by fermentation of whey.

The principal component of the present invention is propionic acid. Today, propionic acid is produced mainly from oil. This is a costly method of production, which also places a burden on the environment in the form of greenhouse gas emissions. There has therefore long been a need to develop production processes for propionic acid that are less harmful to the environment than those used today.

DESCRIPTION OF THE INVENTION

The present invention provides precisely such a method of production through the biological preparation of propionic acid by fermenting whey. Production takes place in a sustainable manner so that the agent is also suitable for organic farming. In what follows the invention will be described in relation to grass silage, but it can also be used in other feeds and byproducts from the food and feed industry, and also animal and vegetable foodstuffs.

The production of cells and metabolites from waste components in the food and feed industry is expected to increase. In particular lactic acid bacteria (LAB) may come to play an essential role via established and new fermentation processes. In recent years there has also been a growing interest in the use of propionic acid bacteria ($2^{nd}$ Int. Symp. on Propionibacteria, Cork, Ireland, 1998). Documented microorganisms such as propionic acid bacteria and lactobacilli accepted for such use (GRAS, Generally Regarded as Safe) are especially preferred for the preservation of, e.g., grass.

In the dairy industry, the greatest challenge is to use make use of the whey that is a byproduct of white cheese and casein manufacture in a sustainable manner. Whey represents both a high pollution burden as organic waste and an interesting byproduct. Whey contains nutritionally valuable proteins that can be used in processed products of various kinds. However, this produces considerable volumes of whey permeate consisting of lactose and salts. Whey permeate can be used as feed for both pigs and ruminant livestock, but will have a reduced feed value because the proteins have been removed. The present invention contributes to a sustainable use of one of the byproducts of agriculture for preserving animal and vegetable products and retaining the feed value in the preservation of grass, so-called silage. The method of production, the product and the use of the aforementioned invention are all considered to be sustainable and environment-friendly, and the product has a good profile as regards health, safety and the environment (HSE).

In what follows we will not distinguish between whey-based products (such as whey permeate), and for the sake of simplicity we shall call all the fractions involved whey.

DESCRIPTION OF THE RELATED ART

The invention relates to a storage-stable preservative containing the natural fermentation products propionic acid and other $C_{1-8}$ monocarboxylic acids, their salts, di- and monosaccharides and live bacteria produced in a sustainable manner. The product will therefore be particularly suitable for organic farming. Furthermore, the propionic acid will have an inhibitive effect on enterobacteria, moulds and yeasts during the actual ensilage of the grass, whilst an addition of specific propionic acid bacteria and lactic acid bacteria with the early production of bacteriocins could inhibit the occurrence of is bacteria such as clostridia in the grass. Clostridia in milk are also known for causing problems in connection with the manufacture of white cheese where clostridia spores from the feed via the milk can cause major financial losses as they spoil the quality of the white cheese.

Surprisingly, in studies of metabolic interactions between immobilised cells of propionic acid bacteria and lactobacilli in bioreactors, it has been found that the biological end product would be highly suitable as an aqueous preservative agent for animal and vegetable products. It would be especially suitable for preserving grass and would have great potential since in some parts of the world silage is the main constituent of the winter diet of ruminant livestock. In organic farming there is at the same time a need for suitable ensiling agents that can be approved in accordance with current requirements as regards ecological means of production.

Northern Europe, Northwest Europe, North America and South and East Asia are regions where there is a substantial preservation of silage. Organic acids are extensively used as preservative agent additives for grass and other crops and for the preservation of byproducts from the food and feed industry. Bacteria and enzymes are also used as ensiling agents for grass and other types of feed, whilst there is only sporadic mention of the use of whey-based ensiling agents in the literature. The plant materials that are preserved by ensilage in Norway generally have a low dry matter content and a low content of water-soluble carbohydrates. Combined with the cold climate in Norway, this gives difficult ensiling conditions. Therefore, it is necessary to use an ensiling agent in order to obtain silage of good quality.

In 1992/1993, Pestalozzi and Mould conducted an experiment at the Saerheim Research Station in Norway where whey was used for the ensilage of grass. They used whey concentrate of about 15% TS containing lactose, whey proteins and salts. High dosage amounts of 40–80 liters per tonne of grass were used. Based on the quality measurements usually used for silo feed such as pH, the content of butyric acid and ammonia-N, the results were not satisfactory. Nonetheless, the feed tests gave equally good results for silage with a whey additive and for formic acid silage. Whey contains a large amount of water and the addition of whey alone gives an unreliable fermentation, which the results obtained by Pestalozzi and Mould also showed with high concentrations of acetic acid. Our invention involving fermentation of the whey containing selected bacteria will give a silage of even better quality.

Swedish Patent Application No. SE 8006718 relates to the fermentation of whey using lactic acid tolerant bacteria cultures prior to concentrating the whey and adding it to grass. There is no mention of the inhibition of undesirable microorganisms in the description. Moreover, the patent is silent with regard to effective production of the mould-inhibiting component propionic acid or antimicrobial components, so-called bacteriocins, produced by propionic acid bacteria and/or lactic acid bacteria. The present invention is a clear improvement over this patent because propionic acid bacteria are used to further ferment the metabolite lactic acid from the lactic acid bacteria that are described in the patent held by Mjölkcentralen Arla. In our invention, propionic acid which has inhibitive effects on undesirable microorganisms typically occurring silage is produced. In addition, we add live propionic acid bacteria to the grass via the ensiling agent both in order to produce propionic acid during the ensilage itself and in order to inhibit undesirable clostridia with effective antimicrobial substances, so-called bacteriocins.

Accordingly, the present invention relates to a preservative agent suitable for animal and vegetable products, characterised in that it has the following composition:

5–30 weight % $C_{1-8}$ monocarboxylic acids;

5–35 weight % fermentable water-soluble carbohydrates;

live cells of propionic acid bacteria and lactic acid bacteria; and water and salts up to 100%.

In addition, the invention relates to a method for producing a preservative agent suitable for animal and vegetable products, characterised in that it consists of the following steps:

(i) forming a substrate consisting of whey, an agent for avoiding microbial contamination and an alkaline buffer;

(ii) fermenting the substrate thus obtained with live cells of propionic acid bacteria and lactic acid bacteria whilst adding a base;

and optionally the steps of:

(iii) concentrating the fermentation product thus obtained and optionally adding more $C_{1-8}$ monocarboxylic acids;

(iv) adding live cells of propionic acid bacteria and/or lactic acid bacteria having antimicrobial activity to the fermentation product thus obtained.

The invention also relates to the use of the preservative agent according to the invention for preserving animal and vegetable products.

The aqueous preservative agent is prepared by a sustainable production process based on the byproduct whey permeate as starting material. The utilisation yield for the whey will be >99.5%.

Whey permeate from ultrafiltration and/or concentrate from nanofiltration are further concentrated by vacuum evaporation to a total dry matter content of 15–25 weight % prior to fermentation. In a continuously stirred bioreactor whey permeate is converted into metabolic products by using free and/or immobilised bacteria. Prior to fermentation in the bioreactor, the bacterial cells are cultivated in a filter fermentor in accordance with Norwegian Patent No. 174589, whilst the continuous bioencapsulation takes place in a bead generator patented in Norway under Patent No. 174588. TINE Norske Meierier BA is proprietor of both these patents.

The biocatalysts are retained in the bioreactor at a constant pH by adding a base and at a constant temperature, whilst the fermentation products and remaining substrate exit the bioreactor via the outlet. As base, a slurry of $Ca(OH)_2$ has been found to be particularly suitable, both because it is pumpable and not least because a supply of $Ca^{2+}$ ensures stable alginate beads. The capacity of the process and the steady state conditions are less dependent upon the specific growth rate of the microorganisms involved compared with a conventional continuous free cell reactor, where a steady state is attained when the specific growth rate is equal to the dilution rate. At the same time, the system protects against contamination by undesirable microorganisms. Therefore, bioencapsulation of relevant bacteria either used in separate beads or mixed in a gel matrix can be employed for such fermentation of whey permeate. However, this does not preclude the use of free cells in a batch or feed-batch reactor.

The invention's use of co-immobilisation and coexistence is particularly useful. When propionic acid bacteria and lactobacilli are used together, the interaction between the bacterial cells can be characterised as commensalism, where one type of bacterium produces an essential substrate for consumption by the other bacterium. The essence of the invention is conversion of lactose to lactic acid by lactobacilli and the subsequent production of propionic acid, acetic acid etc. from the propionic acid bacteria. It is also possible to produce propionic acid direct from lactose (whey) without the presence of lactic acid bacteria.

We have determined that the optimal conditions for the biosynthesis of organic acids from whey permeate are a pH of 6.0 and a temperature of 35° C. with a propionic acid bacteria to lactobacilli cell mass ratio of between 2:1 and 1:1. These conditions give almost equal amounts of lactic acid produced and utilised and a specific productivity for propionic acid of >0.2 g (g dry weight cells)$^{-1}$. h$^{-1}$. The volumetric productivity can typically be optimised by increasing the immobilised cell mass. The release of cells from the gel matrix during continuous fermentation and also insignificant growth in the substrate gives more than 8.00 $\log_{10}$ colony forming units (cfu)/ml of *Propionibacterium* and *Lactobacillus* respectively. The inoculants and/or other added bacterial cells can either be included in the aqueous preservative agent or be dried and stored separately, and mixed with the preservative agent immediately prior to use.

The survival of cells during long-term storage was found to be increased by adding the osmoprotectant glycerol and the repair component casamino acids to the preservative agent. Many additives (polyols, amino acids, amines, polymers and especially carbohydrates) have been found to protect propionic acid bacteria and lactobacilli at low $a_w$, both by controlling cellular water content and by protecting the cell membrane from leakage.

Mass transfer limitations, well known for immobilised systems, led to a mixed lactic acid and lactose consumption in the propionibacteria. A propionic acid reactor concentration of 25 mmole $l^{-1}$ at pH 6.0 and 30° C. typically reduces the specific productivity of propionic acid by 10–20% determined during batch production. Produced propionic acid typically caused reduced activity as a consequence of inhibition. High pH (dissociated acid) due to added alkali, selection and adaptation of bacterial cultures and continuous fermentation reduce the significance of this.

In experiments where we added calcium carbonate to the whey permeate, we observed that the molar ratio of propionic acid to acetic acid increased, whilst we obtained a more stable gel beads, e.g., when Ca alignate was used. The ratio of propionic acid to acetic acid varied considerably depending upon the strain of *Propionibacterium*, aerobic/anaerobic conditions, carbon source and presence of amino acids and citrate. *P. acidipropionici* also gave higher propionic acid yields than *P. freudenreichii*.

Another observation was that potassium sorbate and/or sodium benzoate, typically 0.1–0.5 g/l, reduced the risk of contamination by undesirable microorganisms during the fermentation of the whey permeate in the continuously stirred bioreactor. Sorbate and benzoate are both more effective against moulds and yeasts than against bacteria. A higher proportion of non-dissociated acid (low pH) gives increased inhibition.

Finally, the fermented aqueous preservative agent having a particularly inhibitive effect against moulds, yeasts, enterococci and clostridia can be concentrated by membrane filtration or vacuum evaporation. Membrane filtration is carried out in two steps, nanofiltration and reverse osmosis respectively. The invention gave almost 100% recovery of the water-soluble carbohydrates, 95% recovery of lactic acid and about 70% recovery of propionic acid and acetic acid.

The concentrated additive for preserving silage consists of propionic acid, lactic acid, acetic acid and other organic acids ($C_{1-8}$) and associated salts. Typical dry matter concentration is 400–600 g/l and the pH is typically between 4.5 and 5.5. The concentration of organic acids is typically 50–300 g/l, but also other $C_{1-8}$ monocarboxylic acids and associated salts can be added. The acids are found in both dissociated and non-dissociated form depending upon the pH and respective acid constants. The ensiling agent also contains a mixture of fermentable carbohydrates (lactose, glucose and galactose), 5–35 weight % dry matter based on the weight of the preservative agent.

$CaCO_3$ is added in amounts of 0.1–2.0 weight % dry matter based on the weight of the preservative agent. The agent also contains potassium sorbate and/or sodium benzoate in amounts of 0.025–1.0 weight % dry matter based on the weight of the preservative agent and live cells of respective inoculants in amounts of 6.00 to $11.00_{log\ 10}$ cfu/ml of both *Propionicbacterium* and *Lactobacillus* based on the volume of the preservative agent. The bacterial cells can either be included in the aqueous preservative agent directly or can be cultivated separately, dried and stored separately before being mixed with the agent immediately prior to use. A specific strain of propionibacteria and or lactic acid bacteria producing antimicrobial substances against, inter alia, clostridia and moulds, is included as fermentation organism in the bioreactor or is mixed with the agent prior to use. This produces silage that is free of mould, butyric acid bacteria and butyric acid.

FIG. 5 shows the survival of *Propionibacterium* and *Lactobacillus* in fermented and concentrated whey permeate with 0.1M of glycerol added. The agent was stored at 20° C. and pH 5 for one year without any growth of undesirable microorganisms or the precipitation of salts. Surprisingly, we found that the survival of cells proved to be good during long-term storage in unfavourable conditions. The survival can be enhanced at a low temperature and optimisation of storage conditions whilst the concentration of cells can be increased by admixture directly prior to use. The preservative is also characterised in that it typically contains 0.1–1.0 weight % of both glycerol and casamino acids which act respectively as an osmoprotectant and a repair component during bacterial stress such as long-term storage under unfavourable conditions.

Adding other bacteria, as for instance strains of *Propionibacterium, Lactobacillus, Streptococcus, Lactococcus, Micrococcus, Pediococcus* and/or *Leuconostoc* may be relevant. Enzymes other than those naturally occurring in the grass or that are produced microbially during the grass fermentation may also be added to the grass.

When using fermented whey permeate containing the calcium salts of propionic acid, lactic acid, acetic acid and sugar such as lactose, glucose and galactose, and inoculants (live propionic acid bacteria and lactic acid bacteria) the ensiling agent has the following effect:

1. The live bacteria will immediately start the fermentation of sugar in the added ensiling agent and sugar released from the grass during the formation of propionic acid, lactic acid and some acetic acid. This acid production is more effective than in grass without any additive, and the calcium-neutralised acids in the ensiling agent will not inhibit the development of lactic acid bacteria and propionic acid bacteria at the start. This rapid lowering of pH will first inhibit coliforms (enterobacteria) as shown in FIG. 1 and stop protein degradation in the grass.
2. When the pH of the grass drops into the range of 3.7–4.2, the acid production and the activity of the inoculants will cease. The pH will then be so low that the development of butyric acid bacteria will be inhibited. Propionic acid and lactic acid which are both added to and produced in the grass will now help to inhibit undesirable bacteria because the acids change into a non-dissociated form at a low pH. The addition of these acids also permits good preservation of grass that has too little sugar to ensure reliable preservation based on natural fermentation only. In addition, the use of specific inoculants having bacteriocin effect can increase the effect against, inter alia, butyric acid bacteria and mould.
3. When there are anaerobic conditions in the silage, even quite small amounts of propionic acid and acetic acid will have an inhibitive effect on yeasts. When the silo is opened, the number of yeasts will be lower than if an additive had not been used. This will make the feed more stable and it will take longer before overheating occurs in the silage material. Such overheating takes place when yeasts start aerobic combustion of readily soluble nutriments (lactic acid, sugar etc.)
4. At the same time a reduced loss of silo feed of enhanced quality and increased storage stability (inhibition of moulds, yeasts and spore-forming organisms) take place. The use of this invention will give increased utilisation of local resources.
5. Propionic acid bacteria added via the inoculant will give propionic acid in addition to that added with the ensiling agent, and an effect against mould in the silage can be obtained.
6. In addition to these preserving effects, the ensiling agent will have a net energy value for ruminant livestock that eat the silage with subsequent improved financial result for the producer (milk yield and growth).
7. Increased feed absorption because of the enhanced quality, taste and digestibility of the grass will also take place.

The ensiling agent is sprayed on the plant material when harvesting it into round bales or into a silo or when transferring the grass from a vehicle to a silo. A dosage amount of typically 3–6 liters per tonne of grass will enhance the quality and the biological feed value of the silage.

Organic acids and acidic salts used in an amount of 2–6 kg/tonne of grass have the effect of reducing the pH, thereby reducing plant respiration and proteolysis whilst inhibiting undesirable bacteria such as clostridia, but also inhibiting lactic acid bacteria Nevertheless, in the majority of cases it is the lactic acid fermentation that is the predominant process. Formic acid, usually 85% concentration, is a frequently used silo preservative, mainly because of its effective acidification and antimicrobial effect, according to McDonald et al. 1991, "The Biochemistry of Silage", Second Ed. Chalcombe Publications, Lincoln, UK.

The negative aspect of the use of formic acid, especially when concentrated solutions are used, in that on contact with skin or the eyes, serious injury may occur. Another problem that may occur is corrosion of the grass harvesting equipment. In this area, our invention is in a class by itself out as the corrosion, health, safety and environment aspects are extremely good.

Having conducted preliminary tests, it was established that the preservative agent containing the natural fermentation products propionic acid and other $C_{1-8}$ monocarboxylic acids, their salts, di- and monosaccharides and live bacteria can be produced by the sustainable method of production described.

BRIEF DESCRIPTION OF THE DRAWINGS

The invention and its effects are further elucidated in the following examples, figures and tables. The preservative agent in the following examples has been given the designation FLP.

DESCRIPTION OF THE PREFERRED EMBODIMENTS

EXAMPLE 1

Figure 1:
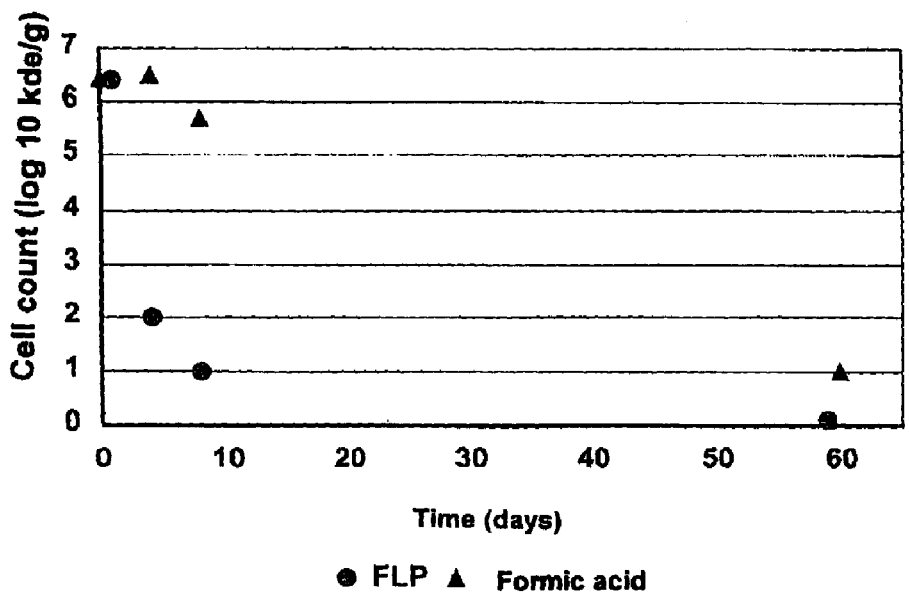
FIG. 1 shows the development in dried grass of coliform bacteria with a dosage of 3 liters of 85% formic acid per tonne of grass and 3 liters of FLP per tonne of grass as 40 weight % in small-scale silos.

This example shows ensilage of directly harvested, predried and thoroughly predried grass in preserving jars. The results are shown in the following table. Sampling from laboratory silos was carried out during storage in an air-sealed package. The jars were stored in a climatic test chamber at 20° C. after adding water for control (3 liters/tonne grass) and synthetically made 40 weight % FLP without bacteria respectively. FLP consisted of ¾ lactose and salts and ¼ organic acids (the ratio 5:1 propionic acid to lactic acid). Calcium carbonate was added as buffer to pH 6.

TABLE 1

| Ensiling agent | Dry matter (%) | pH | NH3-N (% of total N) | Lactic acid (%) | Acetic acid (%) | Ethanol (%) | Butyric acid (%) |
|---|---|---|---|---|---|---|---|
| Directly harvested grass ||||||||
| Control | 13.6 | 3.63 | 8.6 | 1.79 | 0.19 | 0.09 | 0.00 |
| FLP | 12.1 | 3.68 | 6.7 | 1.98 | 0.24 | 0.11 | 0.00 |
| Predried grass ||||||||
| Control | 19.8 | 3.84 | 7.9 | 2.44 | 0.30 | 0.18 | 0.00 |
| FLP | 19.9 | 3.86 | 6.8 | 2.35 | 0.32 | 0.17 | 0.00 |
| Thoroughly predried grass ||||||||
| Control | 31.1 | 4.03 | 7.2 | 2.56 | 0.37 | 0.16 | 0.00 |
| FLP | 30.7 | 4.03 | 6.6 | 2.59 | 0.45 | 0.19 | 0.00 |

As can be seen from Table 1, the prepared silage with added FLP had a slightly lower protein degradation than the controls, but both are considered good on the basis of the ammonia-N content. As we see, the controls without a dosage of ensiling agent are also of good quality. This is ascribable to good grass quality, high lactic acid bacteria content, good harvesting conditions and work well done. The grass had a normal content of water-soluble carbohydrates and low buffer capacity, which suggests that the grass material was relatively easily ensilable. All samples with and without added FLP were free of detectable mould and butyric acid (0%).

EXAMPLE 2

This example shows ensilage of predried grass in round bales. Twelve round bales with FLP and twelve without the additive were ensiled in bags. The results are shown in the following table. The same dosage of 3 liters/tonne of grass of synthetically made 40 weight % FLP without bacteria was used.

TABLE 2

| Ensiling agent | Dry matter (%) | pH | NH3-N (% of total N) | Lactic acid (%) | Acetic acid (%) | Ethanol (%) | Butyric acid (%) |
|---|---|---|---|---|---|---|---|
| Predried grass ||||||||
| Control | 18.2 | 4.50 | 9.5 | 1.19 | 0.51 | 0.12 | 0.00 |
| FLP | 18.0 | 4.50 | 9.2 | 1.25 | 0.45 | 0.09 | 0.00 |

As can be seen from the table, the finished silage with added FLP had almost the same degree of protein degradation as the control, but as we see, the control without a dosage of ensiling agent is also of good quality. This is again due to good grass quality and good ensiling conditions. All samples with and without added FLP were free of butyric acid (0%). The round bales without added FLP all had a distinct layer of mould in the layer between the silage effluent and the grass in the bag. However, no mould could be detected in the twelve round bales to which FLP had been added.

EXAMPLE 3

This example shows ensilage of predried grass in a tower silo. The results are shown in the following table. The same dosage of 3 liters/tonne of grass of synthetically made 40 weight % FLP without bacteria was used. No heat generation was observed in the silo in the respiration phase.

TABLE 3

| Ensiling agent | Dry matter (%) | pH | NH3-N (% of total N) | Lactic acid (%) | Acetic acid (%) | Ethanol (%) | Butyric acid (%) |
|---|---|---|---|---|---|---|---|
| Predried grass ||||||||
| FLP | 25.0 | 4.30 | 8.2 | 1.84 | 0.53 | 0.10 | 0.00 |

As can be seen from Table 3, the finished silage with added FLP was satisfactory as regards the degree of protein degradation. The grass silage was also free of butyric acid (0%) in this case.

EXAMPLE 4

This example shows ensilage of directly harvested and predried grass in preserving jars. The results are shown in the following table. The jars were stored in a climatic test chamber at 20° C. For the control without ensiling agent, water was added in a volume equivalent to 15 weight % FLP with and without bacteria. The additive of 40% weight FLP was added in an amount corresponding to 6 liters/tonne of grass. The FLP consisted of ¾ lactose and salts and ¼ organic acids (the ratio of propionic acid to lactic acid was 1:3). The agent with bacteria contained 8 $\log_{10}$ colony forming units of lactic acid bacteria per ml FLP and <8 $\log_{10}$ cfu propionic acid bacteria per ml FLP.

TABLE 4

| Ensiling agent | Dry matter (%) | pH | NH3-N (% of total N) | Lactic acid (%) | Acetic acid (%) | Ethanol (%) | Butyric acid (%) |
|---|---|---|---|---|---|---|---|
| Directly harvested grass ||||||||
| Control | 17.0 | 3.97 | 5.60 | 2.11 | 0.29 | 0.07 | 0.00 |
| FLP | 17.0 | 3.85 | 5.09 | 2.53 | 0.28 | 0.07 | 0.00 |
| Predried grass ||||||||
| Control | 33.7 | 4.24 | 5.93 | 2.63 | 0.54 | 0.10 | 0.00 |
| FLP | 35.1 | 4.17 | 5.64 | 3.11 | 0.52 | 0.12 | 0.00 |

As can be seen from Table 4, the finished silage with added FLP has a slightly lower degradation of protein than the controls. According to normal evaluation criteria the silage was of good quality, without a trace of butyric acid. As we can see, the controls without a dosage of ensiling agent were also of good quality. Again, this is due to good grass quality, high lactic acid bacteria content, good harvesting conditions and work well done. The grass had a high content of water-soluble carbohydrates, but high buffer capacity, which suggests that the grass material was not as easily ensilable. All samples with and without added FLP were free of detectable mould and butyric acid (0%).

Figure 2:
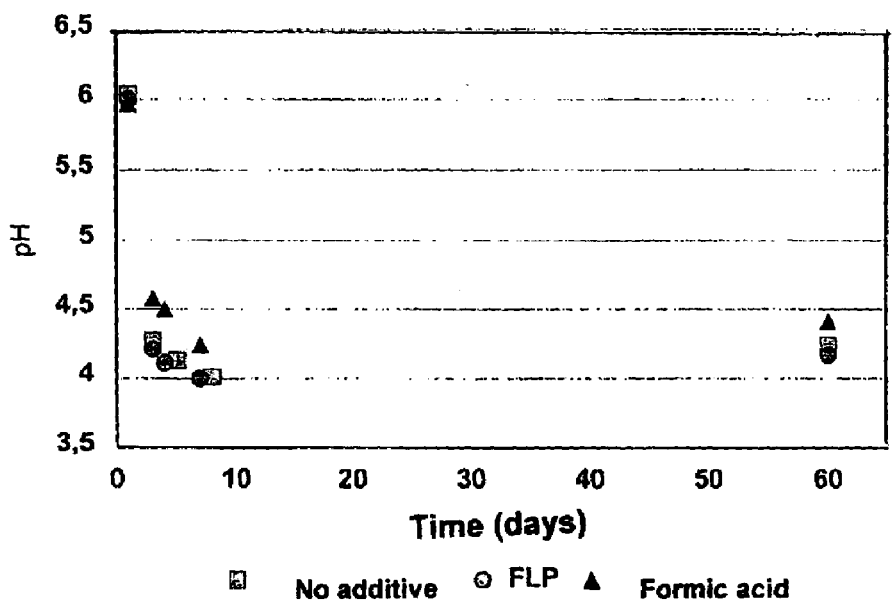
FIG. 2 shows the pH development in dried grass in laboratory silos for a control, formic acid and FLP.

FLP gave a lower pH and higher concentration of lactic acid compared with formic acid and no additive (FIG. 2). More silage effluent was observed for formic acid than on the addition of FLP. A pH <3.7 gives a reduced concentration of soluble carbohydrates, taste and reduced feed absorption. FIG. 2 shows that FLP functions as intended by causing a rapid fall in pH, but not too low a pH. FIG. 1 also shows that 3 liters of FLP (40%) with bacteria per tonne of grass acts as effectively against coliform bacteria as 3 liters of 85% formic acid per tonne of grass.

Figure 3:
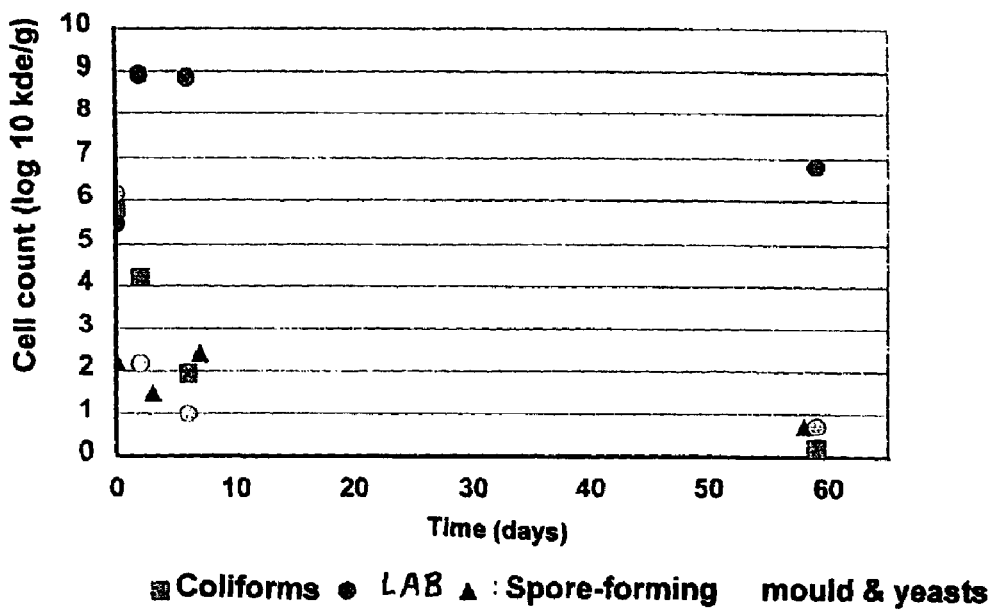
FIG. 3 shows the development in dried grass for coliform bacteria, lactic acid bacteria, anaerobic spore-forming organisms, moulds and yeasts without a dosage of FLP in the small-scale silos.
Figure 4:
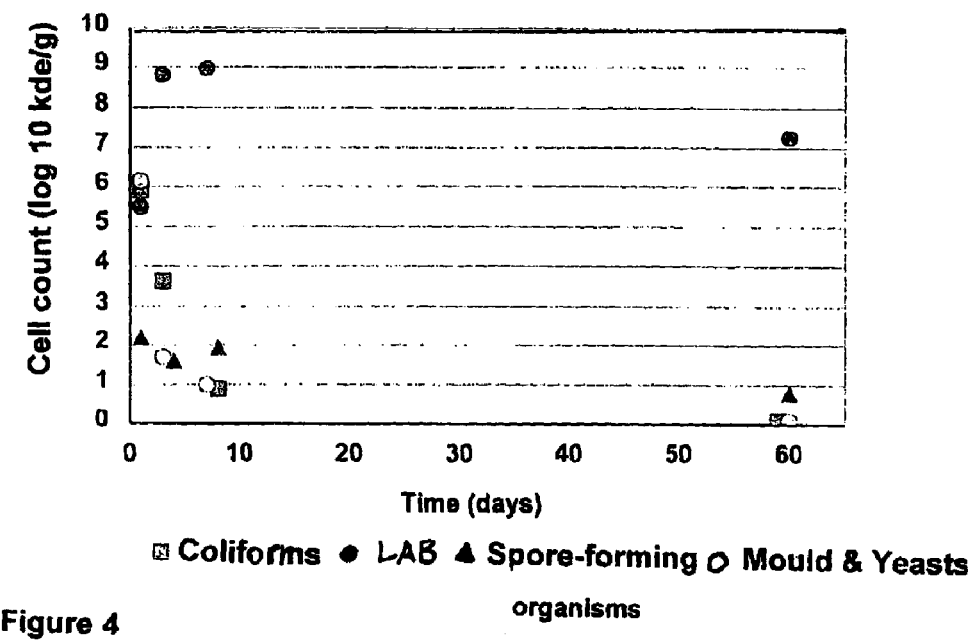
FIG. 4 shows the development in dried grass of coliform bacteria, lactic acid bacteria, anaerobic spore-forming organisms, moulds and yeasts on the dosage of 6 liters of FLP per tonne of grass as 40 weight % in small-scale silos.

FIGS. 3 and 4 show respectively the development of coliform bacteria, lactic acid bacteria, anaerobic spore forming substances, moulds and yeasts in grass without additive (control) and in a grass with added FLP as described above. The development was the same, with some more lactic acid bacteria and slightly fewer coliform bacteria, moulds and yeasts on the addition of FLP after an ensiling period of 60 days. Again, the quality of the grass used in the control was very good.

Figure 5:
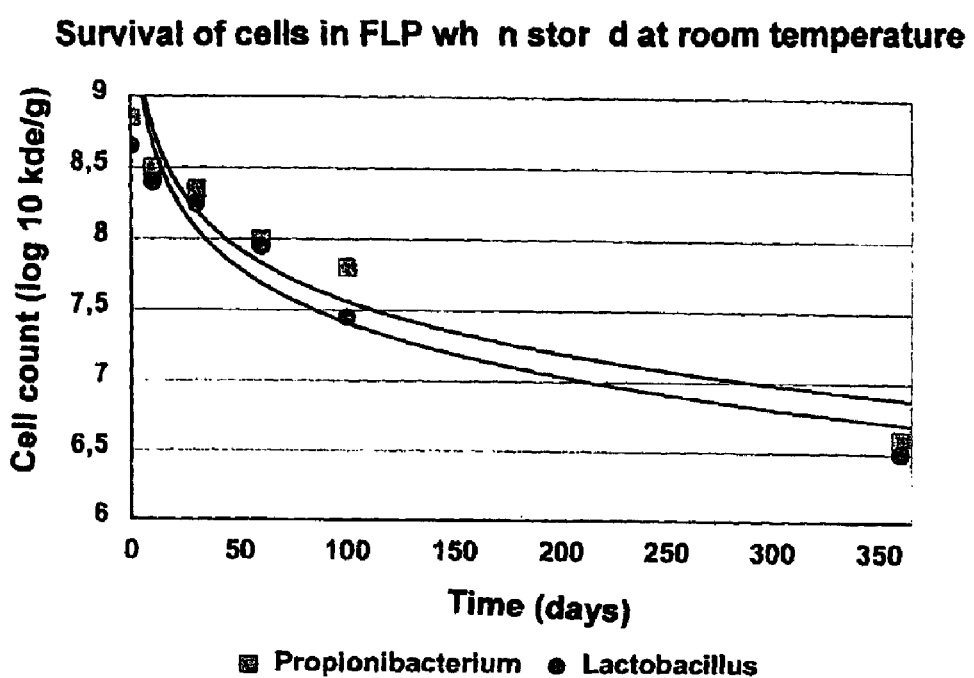
FIG. 5 shows the survival of propionic acid bacteria and lactobacilli in fermented and concentrated whey permeate with added glycerol.

FIG. 5 shows survival as the number of live bacterial cells (colony forming units) of *P. acidipropionici* and *L.b. plantarum* respectively in the ensiling agent for propionic acid bacteria and *lactobacilli*. Typically, 0.1–1.0 weight % glycerol was added to the concentrated and fermented whey permeate at pH 5. The storage study over one year was carried out at 20° C., which is unfavourable as regards survival of bacteria, and at a lower temperature could obviously give increased survival. The addition of amino acids (casamino acids) in other studies have also shown us an increased survival. As can be seen, the number of cfu diminishes by 2 log units during the course of one year in FLP. Without the addition of glycerol the fall was 2–3 log units as early as after 100 days.

Having conducted the tests described above, it was concluded that this aqueous preservative containing the preserving component propionic acid is well suited to preserving animal and vegetable products. The product also contains fermentable water-soluble carbohydrates and live cells of both propionic acid bacteria and lactic acid bacteria which also produce antimicrobial substances with effects against, inter alia, anaerobic spore-forming organisms.

What is claimed is:

1. A method for preparing a preservative agent suitable for animal and vegetable products, comprising the following steps:
   (i) forming a substrate consisting of whey or components of whey, an agent for avoiding microbial contamination and an alkaline buffer;
   (ii) treating the substrate obtained in (i) with alginate beads; and
   (iii) fermenting the substrate obtained in (ii) with live cells of co-immobilized propionic acid bacteria and lactic acid bacteria while adding a base.

2. A method according to claim 1, wherein, in step (i) calcium carbonate is used as alkaline buffer.

3. A method according to claim 1, wherein, in step (iii) a slurried solution of calcium hydroxide ($Ca(OH)_2$) is used as base.

4. A method according to claim 1, wherein, in step (i) benzoic acid and/or sorbic acid are used to avoid microbial contamination.

5. A method according to claim 1, wherein, the live cells of propionic acid and lactic acid bacteria in step (ii) have a concentration of 6.00 to 11.00 $\log_{10}$ cfu/ml of preservative agent.

6. A method according to claim 1, wherein, the fermentation product obtained in step (iv) has a pH of 4.5–5.5.

7. The method of claim 1, comprising the further step of preparing the fermentation product as a preservative agent for preserving animal and vegetable products.

8. The method according to claim 7, wherein the preservation agent is prepared for the ensilage of grass.

9. The method according to claim 1, comprising the further steps of:
   (iv) concentrating the fermentation product thus obtained and optionally adding $C_{1-8}$ monocarboxylic acids; and
   (v) adding live cells of propionic acid bacteria and/or lactic acid bacteria having antimicrobial activity to the thus obtained fermentation product.

10. A method according to claim 9, wherein, step (iv) further comprises adding substances for the survival of bacteria, to the fermentation product.

11. The method of claim 10, wherein the substances are glycerol and casamino acids.

12. The method of claim 1, comprising the further steps of:
   (iv) concentrating the fermentation product thus obtained and adding $C_{1-8}$ monocarboxylic acids; and
   (v) adding live cells of propionic acid bacteria and/or lactic acid bacteria having antimicrobial activity to the thus obtained fermentation product.

13. A method according to claim 12, wherein, the fermentation product obtained in step (iv) is concentrated.

* * * * *